United States Patent
Camacho et al.

(10) Patent No.: US 10,799,502 B2
(45) Date of Patent: Oct. 13, 2020

(54) TREATMENT OR PREVENTION OF NON-INFLAMMATORY NEURONAL DAMAGE FROM BRAIN TRAUMA AND STROKES USING MENTHOL, LINALOOL AND/OR ICILIN

(71) Applicant: NESTEC S.A., Vevey (CH)

(72) Inventors: Susana Camacho, Lausanne (CH); Stephanie Michlig Gonzales, Le Mount-sur-Lausanne (CH); Johannes Le Coutre, Pully (CH); Henry Markram, Lausanne (CH); Maurizio Pezzoli, Lausanne (CH)

(73) Assignee: Societe des Produits Nestle S.A., Vevey (CH)

(*) Notice: Subject to any disclaimer, the term of this patent is extended or adjusted under 35 U.S.C. 154(b) by 0 days.

(21) Appl. No.: 15/462,387

(22) Filed: Mar. 17, 2017

(65) Prior Publication Data

US 2017/0189403 A1 Jul. 6, 2017

Related U.S. Application Data

(62) Division of application No. 14/892,287, filed as application No. PCT/EP2014/060637 on May 23, 2014, now abandoned.

(60) Provisional application No. 61/827,232, filed on May 24, 2013.

(51) Int. Cl.
*A61K 31/513* (2006.01)
*A61K 31/045* (2006.01)
*A23L 33/10* (2016.01)

(52) U.S. Cl.
CPC ............ *A61K 31/513* (2013.01); *A23L 33/10* (2016.08); *A61K 31/045* (2013.01); *A23V 2002/00* (2013.01)

(58) Field of Classification Search
CPC ...... A61K 31/513; A61K 31/045; A23L 33/10
See application file for complete search history.

(56) References Cited

U.S. PATENT DOCUMENTS

| 2010/0137344 A1* | 6/2010 | Fleetwood-Walker ..................... A61K 36/534 514/274 |
| 2012/0172429 A1* | 7/2012 | Woolf .................... A61K 31/00 514/523 |
| 2014/0371276 A1 | 12/2014 | Moriconi et al. |

FOREIGN PATENT DOCUMENTS

| CN | 102512634 | 6/2012 | |
| JP | 2006199647 | 3/2006 | |
| JP | 2007291069 | 8/2007 | |
| KR | 1020090085237 | 8/2009 | |
| KR | 20120103317 | * 9/2012 | ........... A61K 31/045 |
| WO | 03090599 | 11/2003 | |
| WO | 2013168090 | 11/2013 | |

OTHER PUBLICATIONS

Klijn; Stroke; 1997; 28; 2084-2093.*
KR20120103317 published on Sep. 19, 2012; machine translation.*
Miyagi et al. "Acute Therapy for Traumatic Head Injury" Jpn J Rehabil Med, 2013, vol. 50, pp. 557-569.
"Stroke Treatment Guideline 2009", International Medical Information Center Foundation Corporation, 2009, pp. 2-5.
The Japanese Journal of Pharmacology, 2002, vol. 119, pp. 79-88.
Japanese Patent Office Communication for related application No. P2016-514431, Dispatch No. 053246, Dispatch Date Feb. 6, 2018, 12 pages.
Andersson et al. "TRPM8 Activation by Menthol, Icilin, and Cold is Differentially Modulated by Intracellular pH" The Journal of Neuroscience, 2004, vol. 24, No. 23, pp. 5364-5369, XP002519044.
Munoz et al. "Menthol induced hypoxic-ischemic neuroprotection: a potential role for TRPM8 in acute cerebral ischemia" Neuroscience 2008, 4 pages, XP008169908.
Buch et al. "Neuroprotective activity of Cymbopogon martinii against cerebral ischemia/reperfusion-induced oxidative stress in rats" Journal of Ethnopharmacology, 2012, vol. 142, pp. 35-40, XP028519025.
Jiang et al. "The Expression of Menthol on Apoptosis Gene of Brain Tissue of Cerebral Inschemia Reperfusion Injury Model of Rats" Research and Practice of Chinese Medicines, Dec. 31, 205, vol. 19, No. 4, pp. 38-40.
Zakharian et al. "Inorganic Polyphosphate Modulates TRPM8 Channels" Plos One, Apr. 30, 2009, vol. 4, No. 4, pp. e5404 (1-12).
Tanaka et al., "Pathophysiology of Acute Cerebral Ischemia—A Review from a Clinical Viewpoint", J. Jpn. Coll. Angiol., vol. 44, 2004, pp. 217-223.
Kitigawa et al., "Recent Advance of Molecular Investigation in Ishemic Neuronal Damage", Japanese Journal of Stroke, Article in NSOTCHU, vol. 30, Issue No. 6, 2008, pp. 862-868.
Japanese Office Action received for Application No. P2016-514431, dated Jun. 9, 2020, 38 pages.

* cited by examiner

*Primary Examiner* — Pancham Bakshi

(74) *Attorney, Agent, or Firm* — K&L Gates LLP

(57) ABSTRACT

Compositions for prevention or treatment of non-inflammatory neuronal damage from brain trauma and strokes are provided, and the compositions contain a therapeutically effective amount of a compound selected from the group consisting of Menthol, Linalool, Icilin and combinations thereof. Methods for treatment or prevention of non-inflammatory neuronal damage from brain trauma and strokes are also provided, and the methods include administering such compositions.

9 Claims, 5 Drawing Sheets

TREATMENT OR PREVENTION OF NON-INFLAMMATORY NEURONAL DAMAGE FROM BRAIN TRAUMA AND STROKES USING MENTHOL, LINALOOL AND/OR ICILIN

PRIORITY CLAIM

This application is a divisional of U.S. application Ser. No. 14/892,287 filed Nov. 19, 2015, which is a National Stage of International Application No. PCT/EP14/60637 filed May 23, 2014, which claims priority to U.S. Provisional Patent Application No. 61/827,232 filed May 24, 2013, the entire contents of which are incorporated herein by reference.

BACKGROUND

The present inventors surprisingly and unexpectedly found that several active compounds from spices can depress neuronal activity in the neocortex and the amygdala. These compounds are Menthol and Linalool which are transient receptor potential M8 (TRPM8) channel agonists. The present inventors discovered the same effect with Icilin, a synthetic super-agonist of the TRPM8 ion channel, even though the structure of Icilin is not related to Menthol.

Accordingly, in a general embodiment, the present disclosure provides a method for treating non-inflammatory neuronal damage from a condition selected from the group consisting of brain trauma, a stroke and a combination thereof is provided. The method comprises administering to an individual having such damage a composition comprising a therapeutically effective amount of a compound selected from the group consisting of Menthol, Linalool, Icilin and combinations thereof.

In a related embodiment, the composition is selected from the group consisting of a medicament, a food product and a supplement to a food product.

In another embodiment, a method for preventing non-inflammatory neuronal damage from a condition selected from the group consisting of brain trauma, a stroke and a combination thereof is provided. The method comprises administering to an individual having the condition a composition comprising a therapeutically effective amount of a compound selected from the group consisting of Menthol, Linalool, Icilin and combinations thereof.

In a related embodiment, the composition is selected from the group consisting of a medicament, a food product and a supplement to a food product.

In another embodiment, a method for preventing non-inflammatory neuronal apoptosis from a condition selected from the group consisting of brain trauma, a stroke and a combination thereof is provided. The method comprises administering to an individual a composition comprising a therapeutically effective amount of a compound selected from the group consisting of Menthol, Linalool, Icilin and combinations thereof.

In a related embodiment, the composition is selected from the group consisting of a medicament, a food product and a supplement to a food product.

In another embodiment, a method for preventing non-inflammatory neuronal necrosis is provided. The method comprises administering to an individual having the condition a composition comprising a therapeutically effective amount of a compound selected from the group consisting of Menthol, Linalool, Icilin and combinations thereof.

In a related embodiment, the composition is selected from the group consisting of a medicament, a food product and a supplement to a food product.

In another embodiment, a composition for neuroprotection against non-inflammatory neuronal damage from a condition selected from the group consisting of brain trauma, a stroke and a combination thereof is provided. The composition comprises a therapeutically effective amount of a compound selected from the group consisting of Menthol, Linalool, Icilin and combinations thereof.

In a related embodiment, the composition is a medicament.

In a related embodiment, the composition is a food product. The food product can comprise a component selected from the group consisting of protein, carbohydrate, fat and combinations thereof.

In a related embodiment, the composition is a supplement to a food product.

In a related embodiment, the composition is a supplement to a food product.

An advantage of the present disclosure is to provide neuroprotection against non-inflammatory neuronal damage from brain trauma and strokes more effectively and/or more safely than glutamate antagonists.

Another advantage of the present disclosure is to prevent or treat non-inflammatory neuronal damage from brain trauma and strokes.

Still another advantage of the present disclosure is to prevent or treat non-inflammatory neuronal damage from brain trauma and strokes with compounds that can be easily and safely used in food products.

Yet another advantage of the present disclosure is to prevent or treat non-inflammatory neuronal damage from brain trauma and strokes by targeting the pre-synaptic phase of neuronal firing.

An additional advantage of the present disclosure is to prevent or treat non-inflammatory neuronal damage from brain trauma and strokes by targeting the pre-synaptic phase of neuronal firing while reducing the possibility of excitotoxicity.

Another advantage of the present disclosure is to prevent or treat non-inflammatory neuronal damage from brain trauma and strokes with naturally-occurring compounds that can be found in spices.

Still another advantage of the present disclosure is to prevent or treat non-inflammatory neuronal damage from brain trauma and strokes with tolerable side effects or no side effects.

Yet another advantage of the present disclosure is to prevent or treat non-inflammatory neuronal damage from brain trauma and strokes without interfering with the normal action of glutamate under standard conditions Additional features and advantages are described herein, and will be apparent from, the following Detailed Description and the Figures.

DETAILED DESCRIPTION

Figure 1:
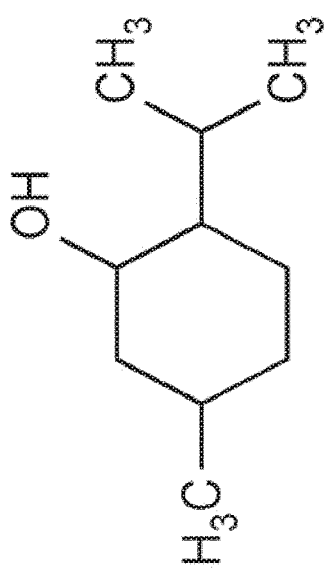
FIG. 1 shows the chemical structures of compounds that can be used in embodiments of the composition according to the present disclosure.
Figure 1:
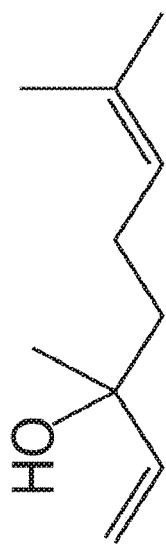
Figure 1:
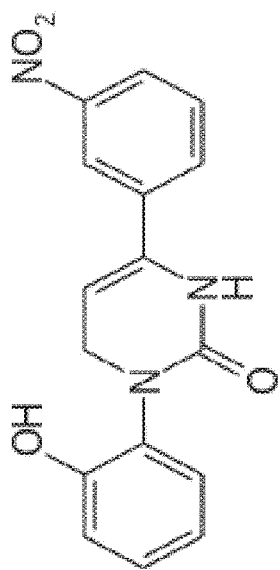

All percentages expressed herein are by weight of the total weight of the composition unless expressed otherwise. When reference is made to the pH, values correspond to pH measured at 25° C. with standard equipment. As used in this disclosure and the appended claims, the singular forms "a," "an" and "the" include plural referents unless the context clearly dictates otherwise. As used herein, "about" is understood to refer to numbers in a range of numerals. Moreover, all numerical ranges herein should be understood to include all integers, whole or fractions, within the range. The food composition disclosed herein may lack any element that is not specifically disclosed herein. Thus, "comprising" includes "consisting essentially of" and "consisting of."

As used herein, "neuroprotection" refers to promotion of neuronal survival, promotion of neuronal repair, limiting neuronal oxidative stress, and/or limiting cell damage. "Cell damage" is any impairment of function in a neuron, including cell death. "Cell death" includes apoptosis and necrosis as non-limiting examples. "Non-inflammatory" means unrelated to or not caused by neurogenic inflammation.

"Prevention" includes reduction of risk and/or severity of non-inflammatory neuronal damage from brain trauma and strokes. The terms "treatment," "treat" and "to alleviate" include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder; and treatment of patients at risk of contracting a disease or suspected to have contracted a disease, as well as patients who are ill or have been diagnosed as suffering from a disease or medical condition. The term does not necessarily imply that a subject is treated until total recovery. The terms "treatment" and "treat" also refer to the maintenance and/or promotion of health in an individual not suffering from a disease but who may be susceptible to the development of an unhealthy condition. The terms "treatment," "treat" and "to alleviate" are also intended to include the potentiation or otherwise enhancement of one or more primary prophylactic or therapeutic measure. The terms "treatment," "treat" and "to alleviate" are further intended to include the dietary management of a disease or condition or the dietary management for prophylaxis or prevention a disease or condition. A treatment can be patient- or doctor-related.

As used herein, a "therapeutically effective amount" is an amount that prevents a deficiency, treats a disease or medical condition in an individual or, more generally, reduces symptoms, manages progression of the diseases or provides a nutritional, physiological, or medical benefit to the individual.

"Animal" includes, but is not limited to, mammals, which includes but is not limited to, rodents, aquatic mammals, domestic animals such as dogs and cats, farm animals such as sheep, pigs, cows and horses, and humans. Where "animal," "mammal" or a plural thereof is used, these terms also apply to any animal that is capable of the effect exhibited or intended to be exhibited by the context of the passage. As used herein, the term "patient" is understood to include an animal, especially a mammal, and more especially a human that is receiving or intended to receive treatment, as treatment is herein defined. While the terms "individual" and "patient" are often used herein to refer to a human, the present disclosure is not so limited. Accordingly, the terms "individual" and "patient" refer to any animal, mammal or human, having or at risk for a medical condition that can benefit from the treatment.

"Food product" and "food composition," as used herein, are understood to include any number of optional additional ingredients, including conventional food additives, for example one or more proteins, carbohydrates, fats, acidulants, thickeners, buffers or agents for pH adjustment, chelating agents, colorants, emulsifiers, excipients, flavor agents, minerals, osmotic agents, a pharmaceutically acceptable carrier, preservatives, stabilizers, sugars, sweeteners, texturizers and/or vitamins. The optional ingredients can be added in any suitable amount.

As set forth above, the present inventors surprisingly and unexpectedly found that several active compounds from spices can depress neuronal activity in neocortex and amygdala. These compounds are Menthol and Linalool which are transient receptor potential M8 (TRPM8) channel agonists. The present inventors discovered the same effect with Icilin, a synthetic super-agonist of the TRPM8 ion channel, even though the structure of Icilin is not related with Menthol; nevertheless, Icilin produces an extreme sensation of cold both in humans and animals. These natural compounds reduce neuronal excitability by 1) increasing the threshold to trigger an action potential and consequently increasing the amount of current required to trigger an action potential in the neocortex; and 2) abortion of action potentials at higher stimulation levels, most likely related to the use-dependent block of Na channels in the neocortex and lateral amygdala. These active compounds change the firing patterns especially at higher stimulation levels where a progressive and dramatic reduction of the action potential (APs) amplitude occurs until complete abortion of APs.

Without wishing to be bound by theory, the inventors believe that the mechanism underlying the selected active compounds of spices, namely Menthol, Linalool and Icilin, solves two main problems compared to neuroprotective glutamate antagonists: 1) Menthol, Linalool and Icilin target a presynaptic phase of APs, decreasing activity and diminishing glutamate release, which reduces drastically the possibility of reaching excitotoxicity levels; and 2) Menthol, Linalool and Icilin act stronger in the high stimulation context. In contrast to glutamate antagonists that typically inhibit the binding of glutamate to NMDA receptors, Menthol, Linalool and Icilin decrease neuronal activity, and target the pre-synaptic phase of the firing to reduce the possibilities of excitotoxicity one step earlier.

Accordingly, the composition provided by the present disclosure comprises a therapeutically effective amount of at least one of Menthol, Linalool or Icilin. The Menthol, Linalool and/or Icilin can be therapeutically effective to provide neuroprotection against non-inflammatory neuronal damage from brain trauma and strokes. Furthermore, Menthol, Linalool and/or Icilin can be therapeutically effective to treat or prevent non-inflammatory neuronal damage from brain trauma and strokes. For example, the composition comprising at least one of Menthol, Linalool or Icilin can be administered to an individual having brain trauma and/or a stroke to prevent or treat non-inflammatory neuronal damage from the brain trauma and/or stroke. The neuroprotection, the treatment or the prevention can reduce or prevent neuronal cell damage, including cell death, such as neuronal apoptosis and/or neuronal necrosis, for example. In an embodiment, the composition comprising a therapeutically effective amount of at least one of Menthol, Linalool or Icilin is administered to a human.

Each of Menthol, Linalool and/or Icilin can be administered to the individual in a daily amount of 0.0015 mg/kg of body weight to 400 mg/kg of body weight, preferably 0.1 mg/kg of body weight to 300 mg/kg of body weight, more preferably 1.0 mg/kg of body weight to 200 mg/kg of body weight, and most preferably 10.0 mg/kg of body weight to 100 mg/kg of body weight. For example, each of Menthol, Linalool and/or Icilin can be administered to the individual in a daily amount of 0.0015 mg/kg of body weight to 0.01 mg/kg of body weight, 0.01 mg/kg of body weight to 0.1 mg/kg of body weight, 0.1 mg/kg of body weight to 1.0 mg/kg of body weight, 1.0 mg/kg of body weight to 10.0 mg/kg of body weight, 10.0 mg/kg of body weight to 100.0 mg/kg of body weight, 100.0 mg/kg of body weight to 200.0 mg/kg of body weight, 200.0 mg/kg of body weight to 300.0 mg/kg of body weight, or 300.0 mg/kg of body weight to 400.0 mg/kg of body weight.

The composition comprising at least one of Menthol, Linalool or Icilin may be a medicament, a food product or a supplement to a food product. The supplement may be in the form of tablets, capsules, pastilles or a liquid, for example. The supplement may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins or the like), adsorbents, carriers, fillers, co-compounds, dispersing agents, wetting agents, processing aids (solvents), flowing agents, taste masking agents, weighting agents, jellifying agents and gel forming agents. The supplement may also contain conventional pharmaceutical additives and adjuvants, excipients and diluents, including, but not limited to, water, gelatin of any origin, vegetable gums, ligninsulfonate, talc, sugars, starch, gum arabic, vegetable oils, polyalkylene glycols, flavoring agents, preservatives, stabilizers, emulsifying agents, buffers, lubricants, colorants, wetting agents, fillers, and the like.

The supplement can be added in a product acceptable to the consumer as an ingestible carrier or support. Non-limiting examples of such carriers or supports are a pharmaceutical, a food composition, and a pet food composition. Non-limiting examples for food and pet food compositions are milks, yogurts, curds, cheeses, fermented milks, milk-based fermented products, fermented cereal based products, milk-based powders, human milks, preterm formulas, infant formulas, oral supplements, and tube feedings.

EXAMPLES

The following non-limiting examples present scientific data developing and supporting the concept of treatment or prevention of non-inflammatory neuronal damage from brain trauma and strokes.

A mouse brain slice was used to study the damage from Menthol, Linalool and Icilin. The amygdaloid complex is located within the medial temporal lobe in neocortex and amygdala. The lateral and basolateral nuclei of the amygdaloid complex receive sensory information from cortical and thalamic structures, process the information, and then transmit the information, either directly or through the basal nucleus, to the central nucleus. For experimental analysis of neuronal activity, synaptic responses from the basolateral complex can be evoked electrically using electrodes, and the action potentials can be measured.

Figure 2:
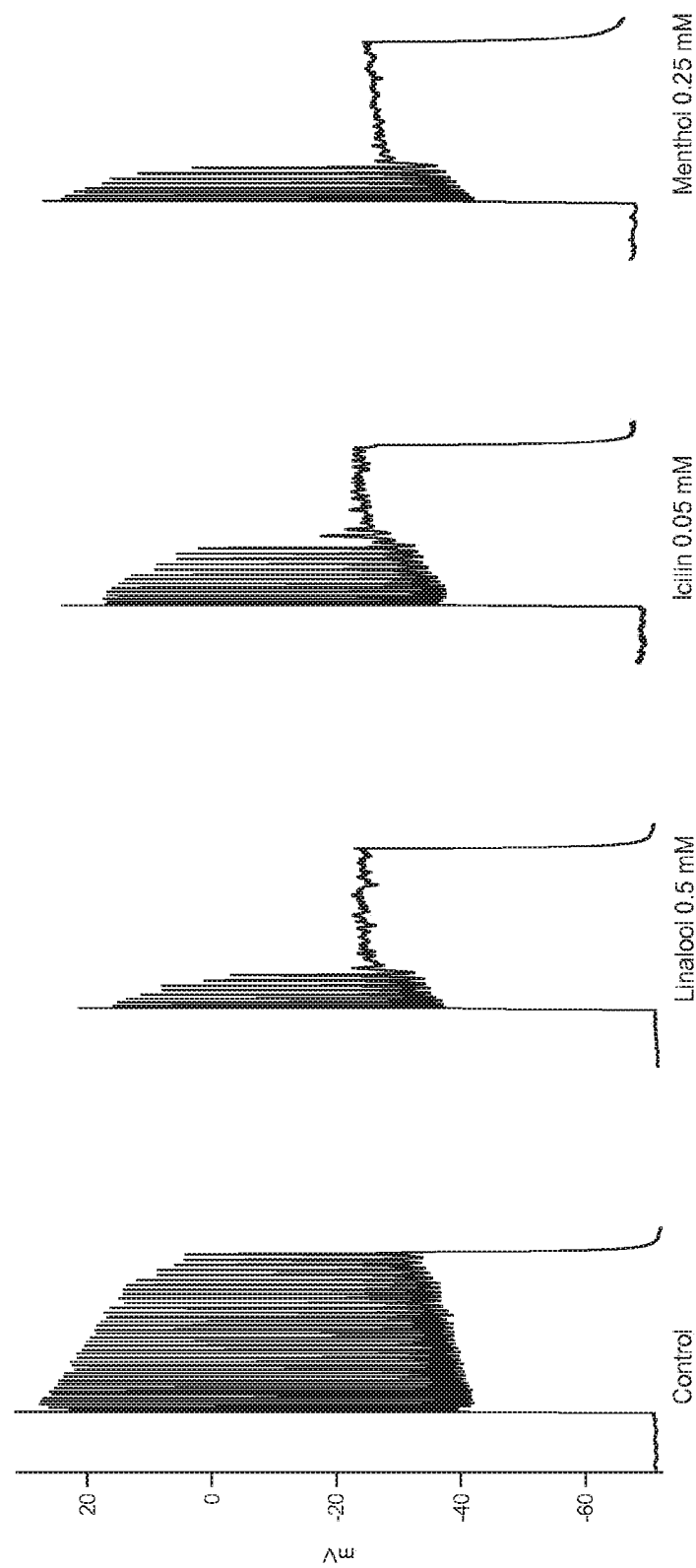
FIG. 2 shows charts of whole cell, current clamp recordings in a Lateral Amygdala glutamatergic neuron (in a mouse brain slice) in the absence (control) and presence of the TRPM8 ligands Linalool, Icilin or Menthol.

FIG. 2 shows recordings in the absence of Menthol, Linalool or Icilin (control) and recordings in the presence of Menthol, Linalool or Icilin. A square pulse of 2.5 s was applied at high depolarization of membrane potential (approximately −30 mV). The recordings show that, in the presence of the TRPM8 ligands at high depolarization levels, inactivation of the sodium fast channels happens sooner relative to control, avoiding further neuronal firing.

Figure 3:
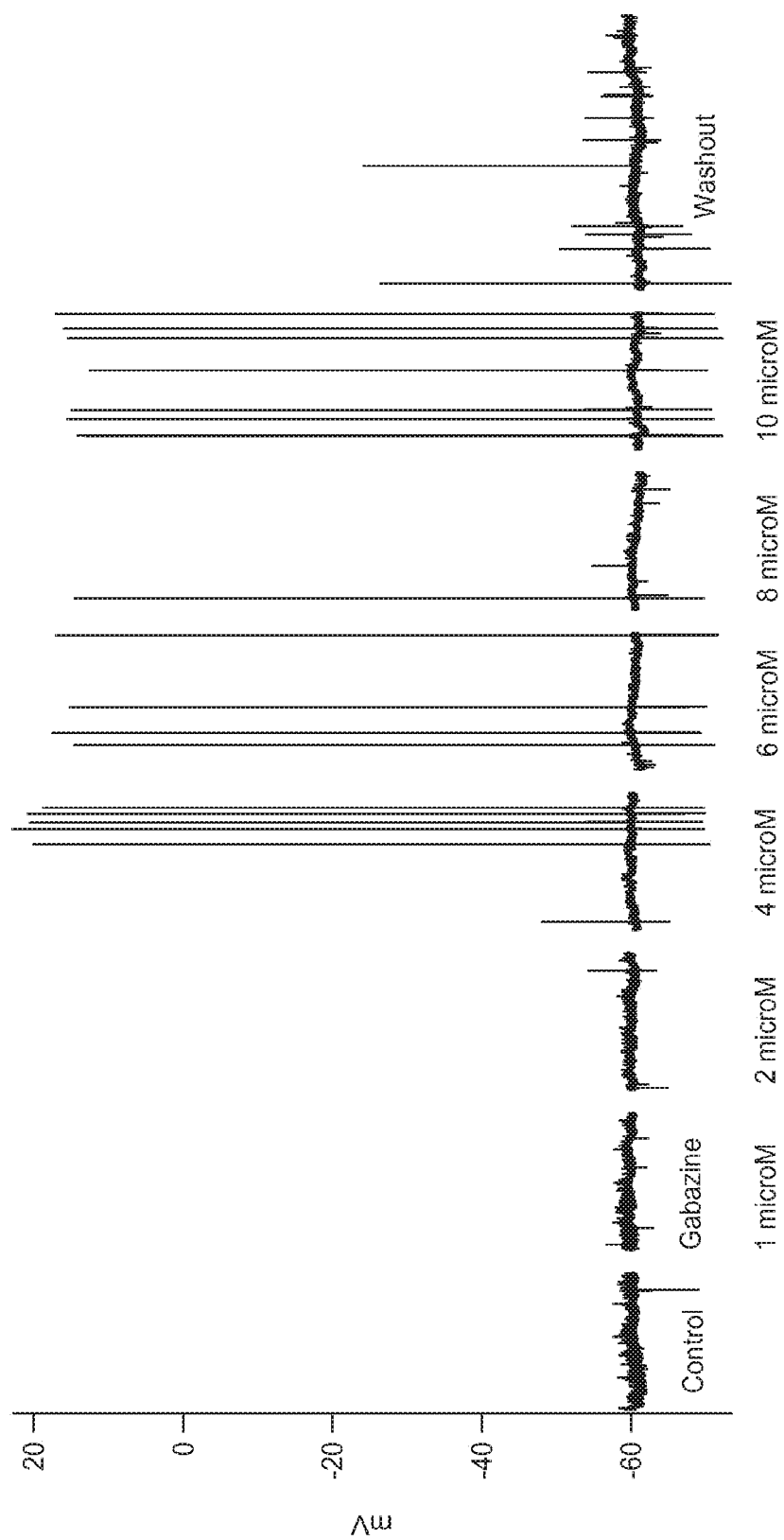
FIG. 3 shows a chart of whole cell, current clamp recordings in a Lateral Amygdala glutamatergic neuron (in a mouse brain slice) with increasing concentration of gabazine (GABAA blocker) applied extracellularly during recordings of 5 min each (washout 10 min).
Figure 4:
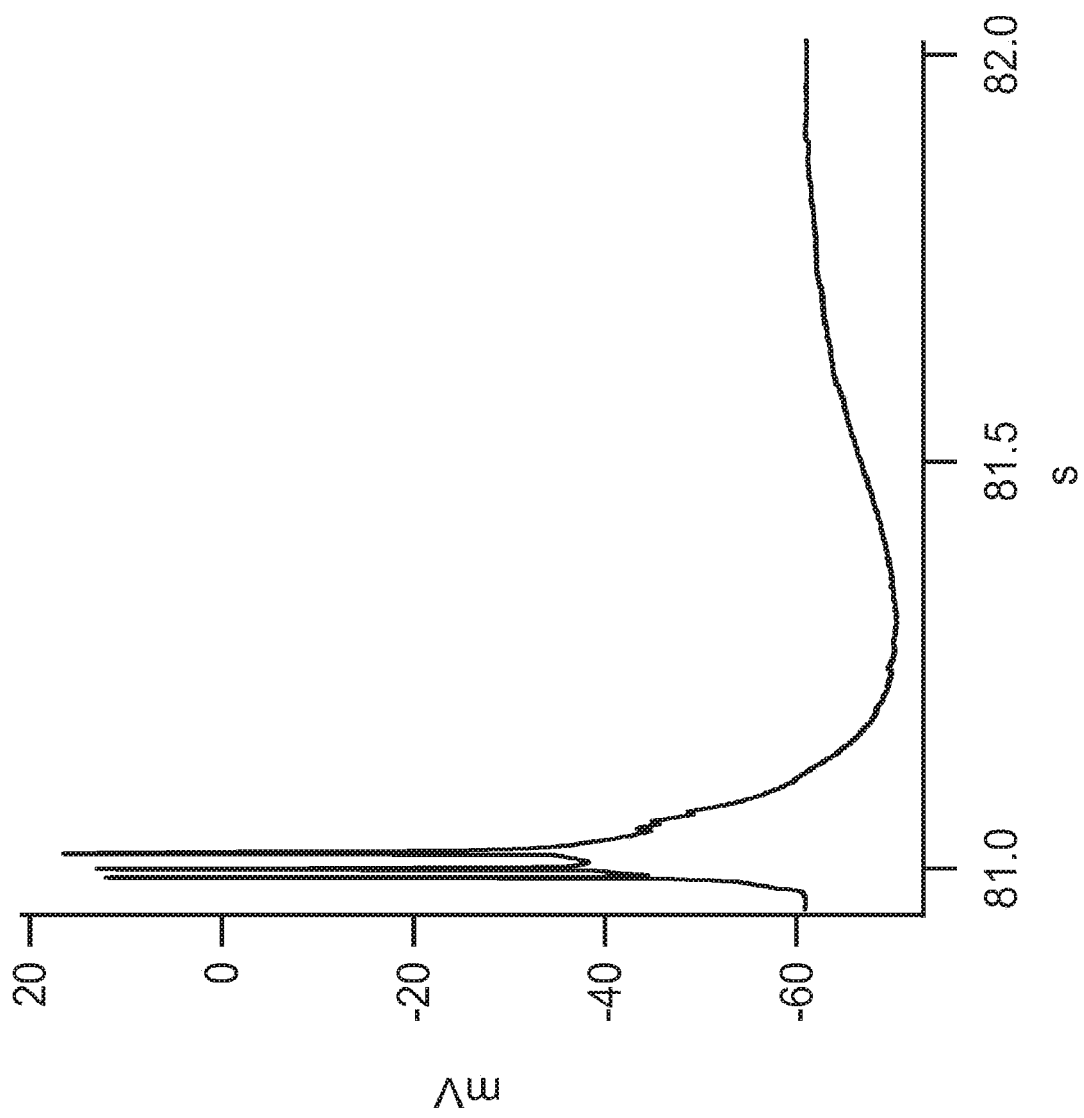
FIG. 4 shows a chart of whole cell, current clamp recordings in a Lateral Amygdala glutamatergic neuron (in a mouse brain slice) showing enhanced detail of a burst.
Figure 5:
FIG. 5 shows a chart of whole cell, current clamp recordings in a Lateral Amygdala glutamatergic neuron (in a mouse brain slice) with increasing concentration of gabazine (GABAA blocker) applied extracellularly during recordings of 5 min each (washout 10 min.) while 10 minutes previous to and during the exposure of the different concentrations of gabazine, 250 AM menthol was also applied extracellularly.

FIG. 3 shows recordings in increasing concentrations of gabazine, a GABA A blocker, applied extracellularly during recordings of 5 minutes each with 10 minute washout. As shown, neurons spontaneously present action potential bursts due to massive presynaptic discharges. FIG. 4 depicts enhanced detail of one of the bursts and shows that serial action potentials can be observed in a single burst. For comparison to FIG. 3, FIG. 5 shows recordings under the same conditions, namely increasing concentrations of gabazine applied extracellularly during recordings of 5 minutes each with 10 minute washout, except that in FIG. 5, Menthol 250 µM was applied extracellularly at 10 minutes previous to and during the exposure of the different concentrations of gabazine. As illustrated in the figure, neurons show a complete absence or a strongly decreased presence of spontaneous bursts (compare FIG. 5 to FIG. 3).

These experimental results demonstrate that Menthol, Linalool and Icilin increase the threshold to trigger an action potential and consequently increase the amount of current required to trigger an action potential in the neocortex, and also abort action potentials at higher stimulation levels.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method of reducing non-inflammatory neuronal cell damage from brain trauma and/or neuronal cell death from brain trauma, the method comprising orally administering a composition to an individual having the brain trauma, the composition comprising a therapeutically effective amount of a compound selected from the group consisting of Linalool, Icilin and combinations thereof, wherein the compound is orally administered to the individual in a daily amount of 0.0015 mg/kg to 400 mg/kg of body weight.

2. The method of claim 1, wherein the composition is selected from the group consisting of a medicament, a food product and a supplement to a food product.

3. The method of claim 1, wherein the individual is a human.

4. The method of claim 1, wherein the composition is a food product comprising a component selected from the group consisting of protein, carbohydrate, fat and combinations thereof.

5. The method of claim 1, wherein the compound is Linalool.

6. The method of claim 1, wherein the compound is Icilin.

7. The method of claim 1, wherein the composition comprises a mixture of compounds of Linalool and Icilin.

8. The method of claim 1, wherein the composition is a food product or a supplement to a food product.

9. The method of claim 1, wherein the neuronal cell death comprises neuronal apoptosis and/or neuronal necrosis.

\* \* \* \* \*